(12) United States Patent
Suzuki et al.

(10) Patent No.: US 10,247,743 B2
(45) Date of Patent: Apr. 2, 2019

(54) ANALYTE TESTING AUTOMATION SYSTEM, BIOLOGICAL SAMPLE CHECK MODULE, AND BIOLOGICAL SAMPLE CHECK METHOD

(71) Applicant: HITACHI HIGH-TECHNOLOGIES CORPORATION, Tokyo (JP)

(72) Inventors: Iwao Suzuki, Tokyo (JP); Tsukasa Suenari, Tokyo (JP); Takahiro Sasaki, Tokyo (JP); Kenichi Takahashi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 82 days.

(21) Appl. No.: 15/031,412

(22) PCT Filed: Oct. 31, 2014

(86) PCT No.: PCT/JP2014/079128
§ 371 (c)(1),
(2) Date: Apr. 22, 2016

(87) PCT Pub. No.: WO2015/072358
PCT Pub. Date: May 21, 2015

(65) Prior Publication Data
US 2016/0266157 A1    Sep. 15, 2016

(30) Foreign Application Priority Data

Nov. 12, 2013  (JP) .................................. 2013-234372

(51) Int. Cl.
| | | |
|---|---|---|
| *G01N 35/02* | (2006.01) | |
| *G01N 35/00* | (2006.01) | |
| *G01N 15/04* | (2006.01) | |
| *G01N 33/49* | (2006.01) | |
| *G01N 15/05* | (2006.01) | |
| *G01N 35/10* | (2006.01) | |

(52) U.S. Cl.
CPC ....... *G01N 35/00732* (2013.01); *G01N 15/04* (2013.01); *G01N 33/491* (2013.01); *G01N 35/00603* (2013.01); *G01N 2015/055* (2013.01); *G01N 2035/1018* (2013.01); *G01N 2035/1025* (2013.01)

(58) Field of Classification Search
None
See application file for complete search history.

(56) References Cited

U.S. PATENT DOCUMENTS

| | | | | |
|---|---|---|---|---|
| 5,734,468 A | * | 3/1998 | McNeal | ................... B01L 3/021 356/244 |
| 2010/0111384 A1 | | 5/2010 | Nagai et al. | |
| 2013/0076882 A1 | | 3/2013 | Itoh | |
| 2013/0123089 A1 | * | 5/2013 | Johns | ................... B01D 21/262 494/37 |

FOREIGN PATENT DOCUMENTS

| | | |
|---|---|---|
| JP | 2000-227399 A | 8/2000 |
| JP | 2004-061137 A | 2/2004 |
| JP | 2007-278707 A | 10/2007 |
| JP | 2010-133925 A | 6/2010 |
| JP | 2012-159481 A | 8/2012 |
| JP | 2013-072806 A | 4/2013 |
| WO | 99/28724 A1 | 6/1999 |
| WO | 2013/002213 A1 | 1/2013 |
| WO | 2013/052318 A1 | 4/2013 |

OTHER PUBLICATIONS

International Search Report of PCT/JP2014/079128 dated Feb. 3, 2015.
International Preliminary Report on Patentability received in corresponding International Application No. PCT/JP2014/079128 dated May 26, 2016.
European Search Report received in corresponding European Application No. 14861651.9 dated May 12, 2017.

* cited by examiner

*Primary Examiner* — Paul S Hyun
(74) *Attorney, Agent, or Firm* — Mattingly & Malur, PC (57) ABSTRACT

The type of blood collection tube (1) inserted into this system is automatically recognized, a lifting operation for checking the state and volume of analyte is switched on the basis of the automatic recognition result, a mechanical operation parameter based on the blood collection tube type is determined, and the blood collection tube (1) is grasped and lifted. Then, an image processing threshold is changed on the basis of the automatic recognition result, and image processing is performed using a threshold parameter based on the blood collection tube type to check the state and volume of the analyte. This enables precise automatic checking of the state and/or volume of the analyte for various types of blood collection tubes.

15 Claims, 8 Drawing Sheets

| CONTAINER TYPE NO. | | CONTAINER | | | | | | | 11A {GRIPPING POSITION DROP VALUE / GRIPPING POSITION ELEVATION VALUE} | | | | 11B {NORMAL, HEMOLYTIC THRESHOLD VALUE / LIPIDEMIA THRESHOLD} | | | | | | | | | | | | | | | | SEPARATING MATERIAL | | |
|---|---|---|---|---|---|---|---|---|---|---|---|---|---|---|---|---|---|---|---|---|---|---|---|---|---|---|---|---|---|---|
| | | | | | PLUG TYPE | R | G | B | mm | PULSE | mm | PULSE | LOW | | | | HIGH | | | | LOW | | | | HIGH | | | | TYPE | HEIGHT | INNER DIAMETER |
| No | NAME | LENGTH | DIAMETER | | | | | | | | | | h | s | v | h | s | v | h | s | v | h | s | v | | | |
| 1 | COMPANY A 13x75 GEL RUBBER | 75 | 13 | RUBBER | 255 | 0 | 255 | 40.3 | 1400 | 40.3 | 1400 | 0 | 220 | 130 | 100 | 255 | 255 | 0 | 50 | 250 | 100 | 800 | 255 | GEL | 10.3 | 12.9 |
| 2 | COMPANY A 13x100 GEL RUBBER | 100 | 13 | RUBBER | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 3 | COMPANY A 16x100 GEL RUBBER | 100 | 16 | RUBBER | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 4 | COMPANY A 13x75 GEL RUBBER | 75 | 13 | HEMOGARD | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 5 | COMPANY A 13x100 GEL RUBBER | 100 | 13 | HEMOGARD | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 6 | COMPANY A 16x100 GEL RUBBER | 100 | 16 | HEMOGARD | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 7 | COMPANY B 16x100 GEL RUBBER | 100 | 16 | RUBBER | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 8 | COMPANY B 16x100 WHITE GEL RUBBER | 100 | 16 | HEMOGARD | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 9 | COMPANY C 13x75 GEL RUBBER | 75 | 13 | RUBBER | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 10 | COMPANY C 13x100 GEL RUBBER | 100 | 13 | HEMOGARD | XXX | XXX | XXX | XXX | YYYY | XXX | YYYY | HHH | SSS | VVV | HHH | SSS | VVV | HHH | SSS | VVV | HHH | SSS | VVV | GEL | XXX | YYY |
| 11 | COMPANY C 13x100 BEADS SCREW | 100 | 13 | SCREW | XXX | XXX | XXX | XXX | YYYY | XXX | YYYY | HHH | SSS | VVV | HHH | SSS | VVV | HHH | SSS | VVV | HHH | SSS | VVV | BEADS | XXX | YYY |

ANALYTE TESTING AUTOMATION SYSTEM, BIOLOGICAL SAMPLE CHECK MODULE, AND BIOLOGICAL SAMPLE CHECK METHOD

TECHNICAL FIELD

The present invention relates to an analyte testing automation system, a biological sample check module, and a biological sample check method for automatically checking the state and volume of an analyte which can be used in the analyte testing automation system for clinical laboratory tests.

BACKGROUND ART

For example, Patent Literature 1 discloses the technology for capturing the image of a blood collection tube with a camera, comparing the captured image of the blood collection tube with a black and white color calibration result to distinguish the type of analyte container by a matching process, and calculating the liquid volume after determining the bias value as the technology for realizing an analyte check function.

CITATION LIST

Patent Literature

Patent Literature 1: WO1999-28724

SUMMARY OF INVENTION

Technical Problem

Recently, the integration of an analyte check function in which the volume of serum obtained by centrifuging the analyte being used and the state of the analyte after centrifugation are automatically verified in an analyte testing automation system which performs pretreatments such as dispensing to perform biochemical analyses or immunoassays of analytes such as blood and urine has been sought in the field of clinical laboratory examinations.

Regarding the state of the analyte after centrifugation, other than the normal state, the analyte may be in a hemolytic state, a chylous state, or an icteric state. An analyte in an abnormal state cannot be used in analysis, thus, redrawing is necessary, and accordingly, it is necessary to discriminate an analyte which is in an abnormal state.

Conventionally, analyte checking operations such as the verification of the serum volume and the discrimination of abnormal analytes was performed visually by a laboratory technician, thus, the efficiency was poor. Therefore, the automation of the checking operation has been desired, and the integration of the analyte check function in a pretreatment system has been sought.

There are numerous types of blood collection tubes which are used in analyte testing automation systems. For example, not only are there differences in the shape such as the length of the tube and the inner diameter of the tube, but there are also differences in the materials such as plastic or vinyl, thus, there are colored and transparent tubes and milky-white clouded tubes (white translucent).

More specifically, in the case of a milky-white blood collection tube, the contents of the blood collection tubes can be observed from the outside through the wall, but with respect to the color of the serum portion of the result from the image captured by a camera, the white color is emphasized compared to transparent blood collection tubes, thus, the risk for incorrectly verifying the state of the analyte was high. Further, the verification of the interface between the serum and the white gel-like separating agent is difficult, thus, the risk of incorrectly verifying the volume of serum was high.

Taking the aforementioned problems into consideration, Patent Literature 1 specifies a method for calibrating each of the blood collection tubes to be used, setting the presence of a gel-like separating agent, and automatically verifying a blood collection tube, but the information of the color of the blood collection tube itself has not been managed, thus, the problem regarding an incorrect verification in the same manner as stated above cannot be averted.

Further, the method of Patent Literature 1 requires that the calibration of each of the blood collection tubes to be used be performed by the user, thus, there is the problem that calibration requires much time and effort.

An object of the present invention is to provide an analyte testing automation system, a biological sample check module, and a biological sample check method which can precisely and automatically check the state and volume of an analyte even if numerous types of blood collection tubes are used.

Solution to Problem

The configurations described in, for example, the claims are used to solve the aforementioned problems.

The present invention includes a plurality of means for solving the aforementioned problems, and one example is an imaging unit for capturing an image from the side of a container containing a biological sample, a container type specification unit for obtaining information specifying the type of container, and a control unit having a processing unit for processing an image captured by the imaging unit on the basis of the parameters in accordance with the container type specified by the container type specification unit and a discrimination unit for discriminating the state of the contents within the container on the basis of the processing by the processing unit.

Advantageous Effects of Invention

According to the present invention, the user can automatically and precisely perform the checking of the state and volume of the analyte by only setting numerous types of blood collection tubes in the loading position without considering the differences in color such as from a transparent tube to a milky-white clouded tube and the different shapes of blood collection tubes such as the length of the tune and the inner diameter of the tube, and the user can load the blood collection tubes in the analyte testing automation system without the necessity of performing operations which require time and effort such as calibration.

DESCRIPTION OF EMBODIMENTS

The embodiments of the analyte testing automation system, the biological sample check module, and the biological sample check method of the present invention will be explained below using the drawings.

<First Embodiment>

A first embodiment of the analyte testing automation system and the biological sample check method of the present invention will be explained using FIGS. 1 to 11.

Figure 1:
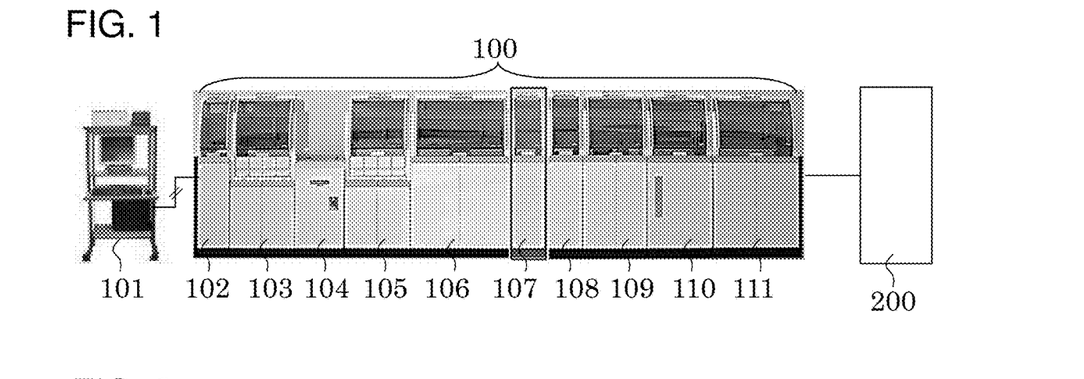
FIG. 1 is a drawing showing an example of the outer appearance of the analyte testing automation system in a first embodiment of the present invention.
Figure 2:
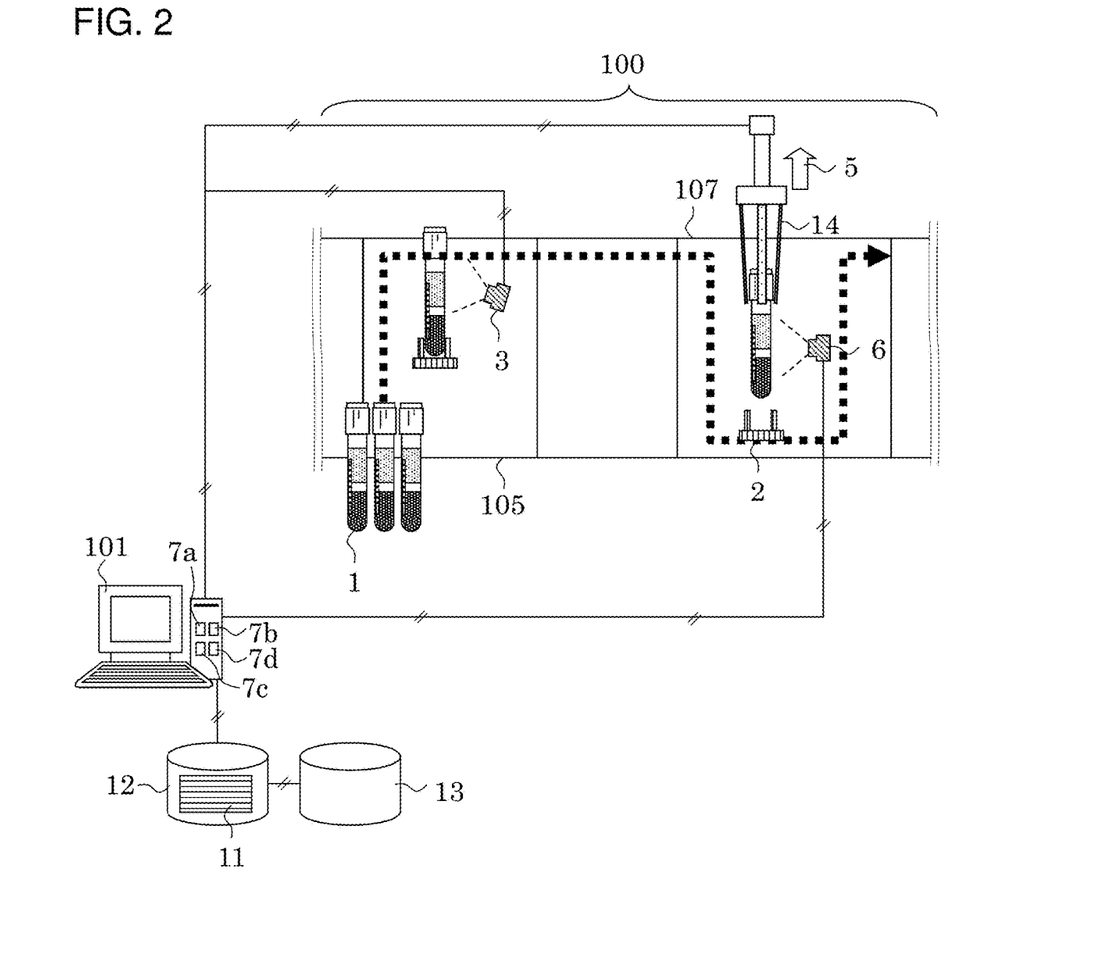
FIG. 2 is a drawing showing an overview of the configuration of the analyte testing automation system in the first embodiment of the present invention.
Figure 3:
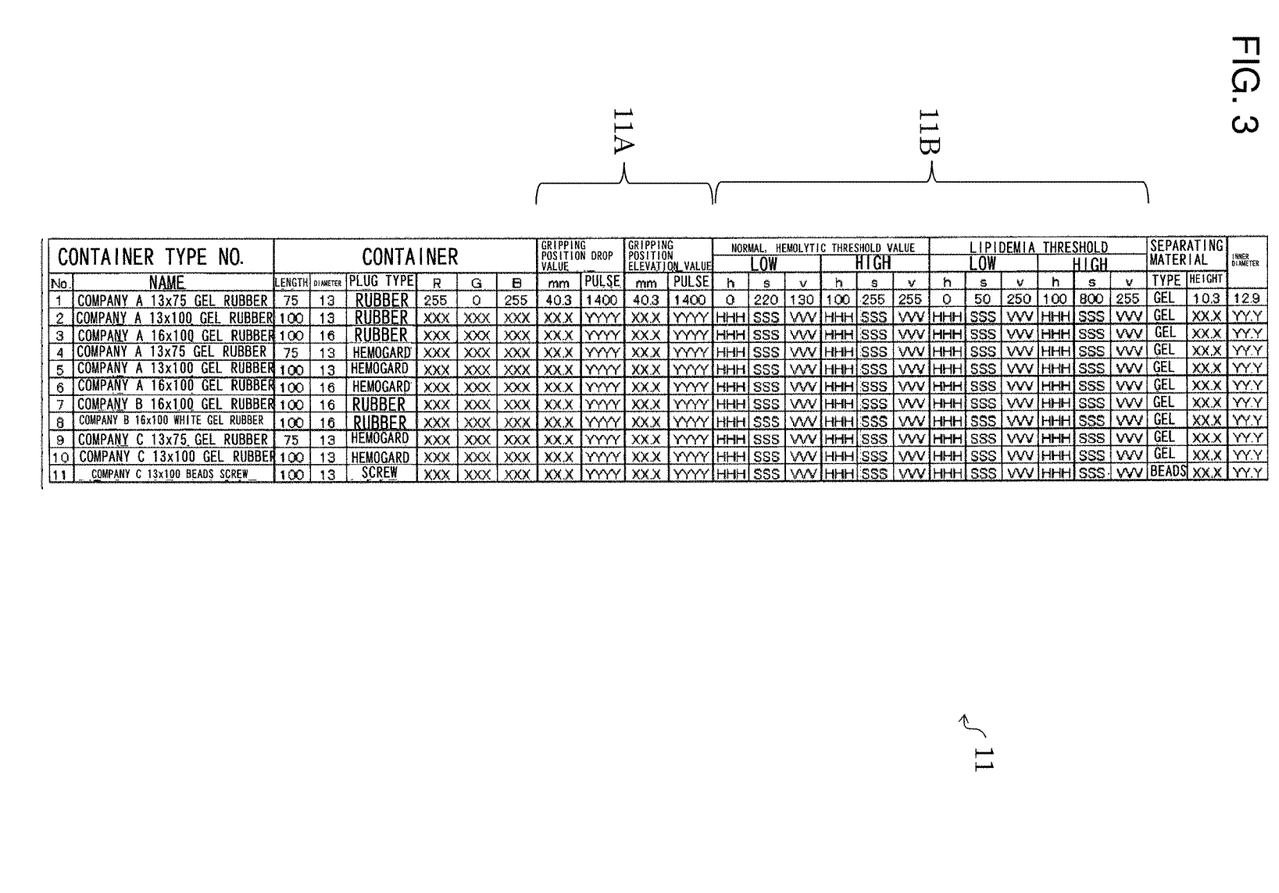
FIG. 3 is a drawing showing an example of the lifting operation parameters and the threshold parameters in accordance with the analyte container type which are recorded in the database of the analyte testing automation system in the first embodiment of the present invention.
Figure 4:
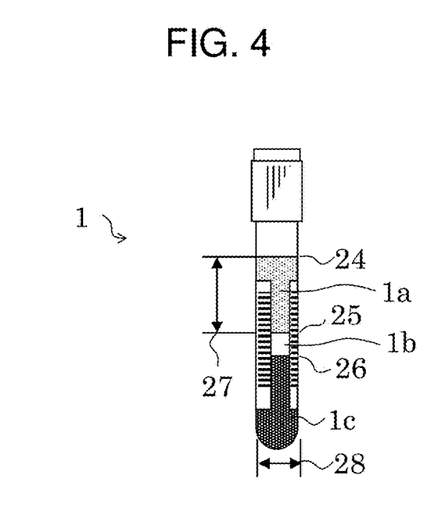
FIG. 4 is a drawing showing an example of the overview of the analyte container to be checked by the analyte testing automation system in the first embodiment of the present invention.
Figure 5:
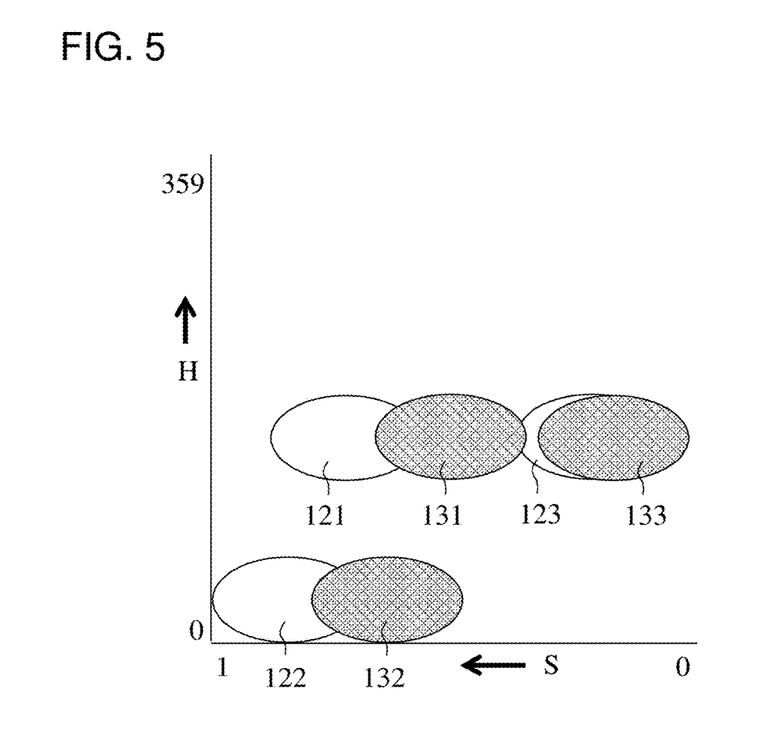
FIG. 5 is a drawing describing an overview of the differences in the threshold parameters in the analyte containers in the analyte testing automation system in the first embodiment of the present invention.
Figure 6:
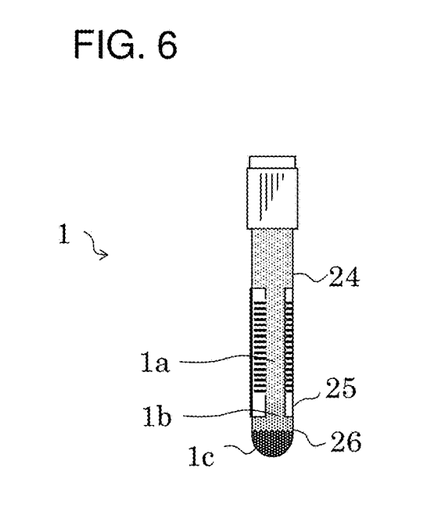
FIG. 6 is a drawing showing another example of the overview of the analyte container to be checked by the analyte testing automation system in the first embodiment of the present invention.
Figure 7:
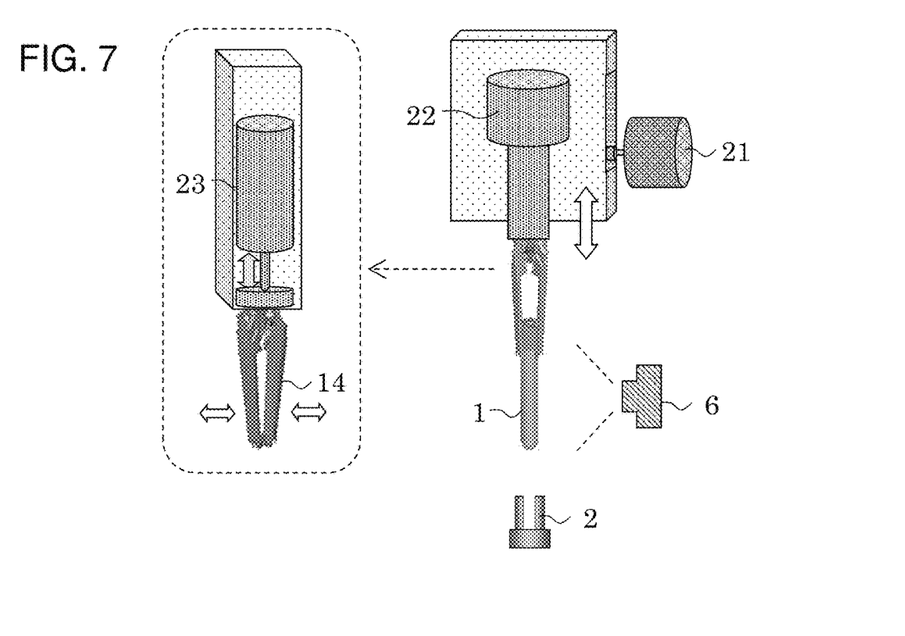
FIG. 7 is a drawing describing an overview of the analyte container lifting and rotating mechanisms in the first embodiment of the present invention.
Figure 8:
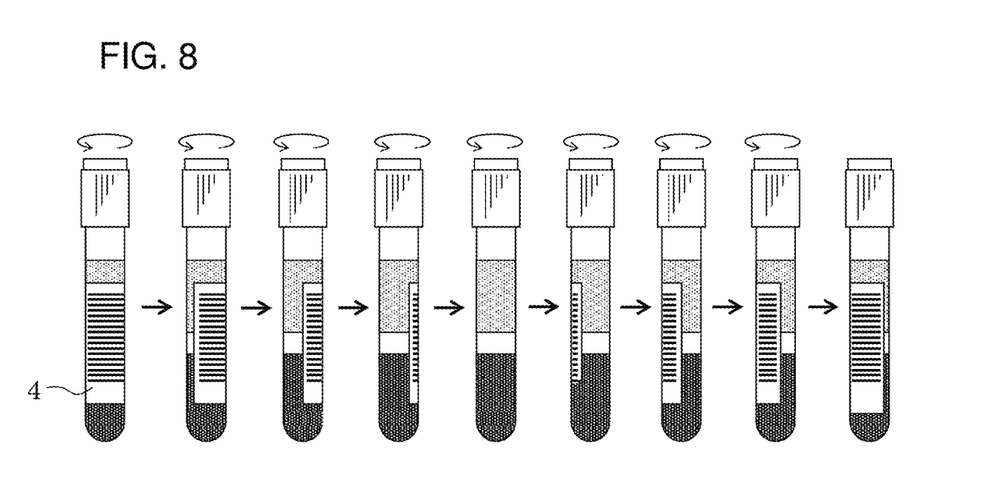
FIG. 8 is a drawing showing the state of the rotation of the overview of the analyte container to be checked by the analyte testing automation system in the first embodiment of the present invention.
Figure 9:
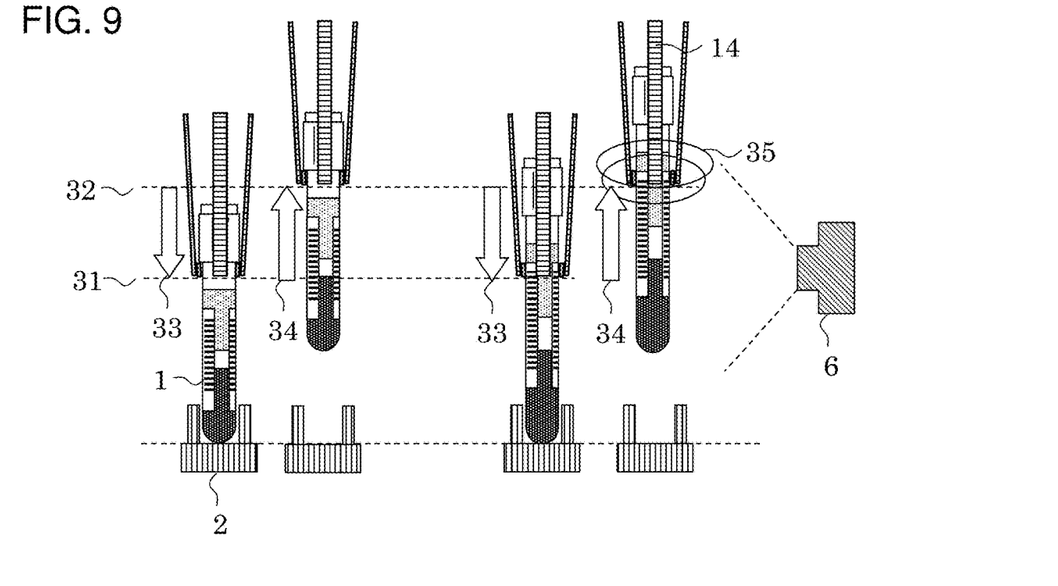
FIG. 9 is a drawing showing an example of the lifting of the analyte container for comparison.
Figure 10:
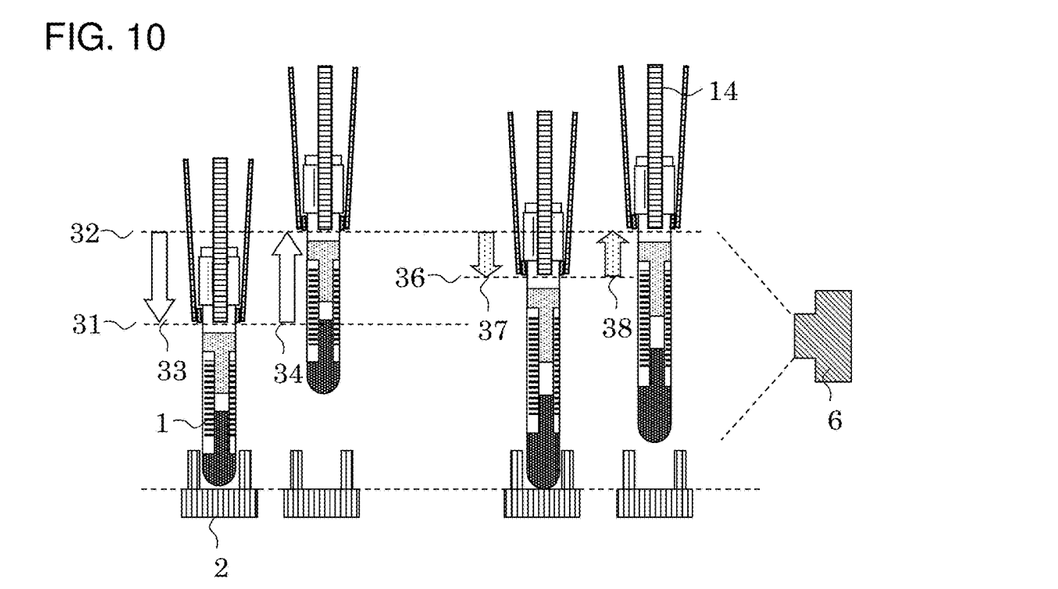
FIG. 10 is a drawing showing an example of the lifting of the analyte container by the analyte testing automation system in the first embodiment of the present invention.
Figure 11:
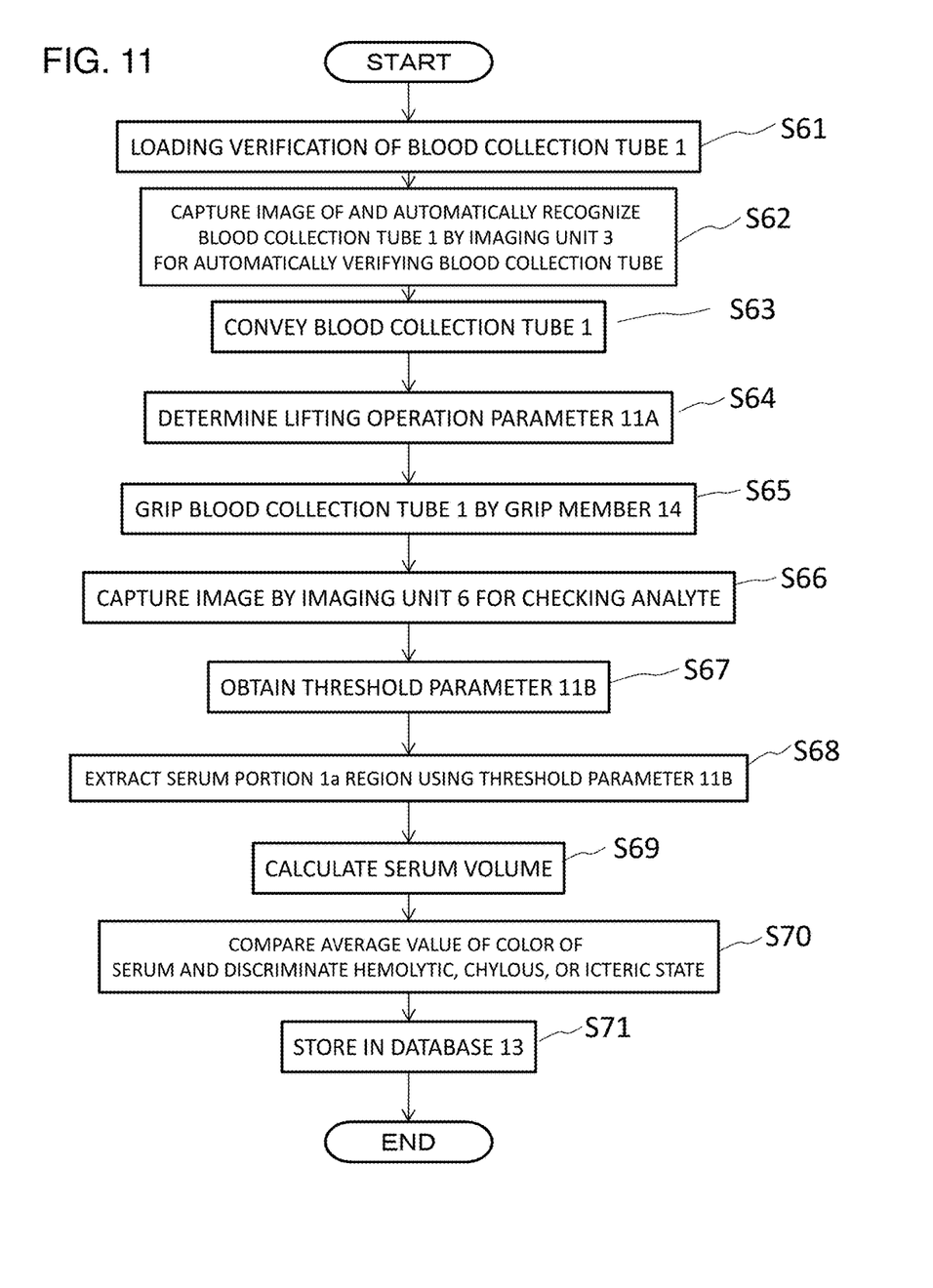
FIG. 11 is a flowchart of the control of the analyte testing automation system in the first embodiment of the present invention.

FIG. 1 is a drawing showing an example of the outer appearance of the analyte testing automation system in the first embodiment of the present invention, FIG. 2 is a drawing showing an overview of the configuration of the analyte testing automation system in the first embodiment of the present invention, FIG. 3 is a drawing showing an example of the lifting operation parameters and the threshold parameters in accordance with the analyte container type which are recorded in the database of the analyte testing automation system in the first embodiment of the present invention, FIG. 4 is a drawing showing an example of the overview of the analyte container to be checked by the analyte testing automation system in the first embodiment of the present invention, FIG. 5 is a drawing describing an overview of the differences in the threshold parameters in the analyte containers in the analyte testing automation system in the first embodiment of the present invention, FIG. 6 is a drawing showing another example of the overview of the analyte container to be checked by the analyte testing automation system in the first embodiment of the present invention, FIG. 7 is a drawing describing an overview of the analyte container lifting and rotating mechanisms in the first embodiment of the present invention, FIG. 8 is a drawing showing the state of the rotation of the overview of the analyte container to be checked by the analyte testing automation system in the first embodiment of the present invention, FIG. 9 is a drawing showing an example of the lifting of the analyte container for comparison, FIG. 10 is a drawing showing an example of the lifting of the analyte container by the analyte testing automation system in the first embodiment of the present invention, and FIG. 11 is a flowchart of the control of the analyte testing automation system in the first embodiment of the present invention.

In FIG. 1, the analyte testing automation system for checking the biological sample (analyte) housed in the blood collection tube 1 is constructed from an analyte pretreatment system 100 including a plurality of modules including an analyte loading unit 105, a centrifuge unit 106, an analyte checker 107, an opening unit 108, an aliquot sample test tube preparation unit 109, a dispensing part 110, a transfer unit 111, a plug part 102, an analyte storage unit 103, and an empty holder stocker part 104 as the basic elements, and an operation control unit 101 for controlling the entirety of the analyte pretreatment system 100.

An automatic analyzer 200 for performing the qualitative and quantitative analysis of the components in the analyte is connected at the end of the analyte pretreatment system 100.

The analyte loading unit 105 is a module for loading a blood collection tube 1 in which an analyte is stored in the analyte pretreatment system 100. The centrifuge unit 106 is a module for centrifuging the loaded blood collection tube 1. The opening unit 108 is a module for opening the plug of the blood collection tube 1. The aliquot sample test tube preparation unit 109 is a module for performing the preparations necessary in order to dispense the loaded analyte in the dispensing part 110. The dispensing part 110 is a module for dispensing the centrifuged analyte so that it may be analyzed by an automatic analyzer 200, etc., and attaching a barcode, etc., to the dispensed container. The transfer unit 111 is a module for classifying the dispensed analyte container, and preparing to transfer to the automatic analyzer 200. The plug part 102 is a module for closing the plug in the container and the tube. The analyte storage unit 103 is a module for storing the closed container and tubes. The operation control unit 101 controls each module in the analyte pretreatment system 100 and the operation of each mechanism in each module.

Next, the analyte checker 107 and the configurations related to the analyte checker 107 in the analyte testing automation system of the embodiment will be explained with reference to FIG. 2.

In FIG. 2, the analyte checker 107 includes the imaging unit 6 for analyte checking and a grip member 14. The imaging unit 6 for analyte checking and the grip member 14 are communicatively coupled to the operation control unit 101.

Further, the analyte checker 107 is communicatively coupled to a first image processing unit 7a, a calculation unit 7b, a second image processing unit 7c, and a discrimination unit 7d provided in the operation control unit 101. The operation control unit 101 is further communicatively coupled to an imaging unit 3 for automatically verifying the blood collection tube provided in the analyte loading unit 105.

The imaging unit 3 for automatically verifying the blood collection tube is a camera for capturing images of the blood collection tube 1 which was loaded in the analyte loading unit 105.

The operation control unit 101 is communicatively coupled to a database 12 and a database 13. As shown in FIG. 3, the various parameters 11 for each type of blood collection tube 1 such as the lifting operation parameter 11A and the threshold parameter 11B in accordance with the type of blood collection tube 1 are stored in advance in the database 12. The check result of the analyte in the blood collection tube 1 and all of the data used in the check are stored in the database 13.

As shown in FIG. 3, the various parameters 11 for each type of blood collection tube 1 are stored in a text-based table form, thus, visualization is possible and the correction and addition of parameters is easy. Further, the parameter 11 can be preset by the numerous device manufacturers in accordance with the type of blood collection tube 1 at the time the device is shipped, and thus, is already stored in the database 12.

Returning to FIG. 2, the first image processing unit 7a of the operation control unit 101 specifies the type of blood collection tube 1 by automatically verifying the type of blood collection tube by the outer appearance of the blood collection tube 1 and the color of the cap on the basis of the captured image in the imaging unit 3 for automatically verifying the blood collection tube. The specific method, for example, is a method including a database obtained by photographing a container to be used in advance, and which performs matching with the captured image.

The first image processing unit 7a transmits the obtained information to the operation control unit 101. The information of the diameter of the blood collection tube 1 is used when calculating the volume such as of the serum portion 1a in the discrimination unit 7d.

The specification step for specifying the type of blood collection tube 1 is performed by the first image processing unit 7a and the imaging unit 3 for automatically verifying the blood collection tube.

The calculation unit 7b of the operation control unit 101 determines the lifting operation parameter 11A most suitable for the type of blood collection tube 1 specified in the first image processing unit 7a from each of the lifting operation parameters 11A in accordance with the type of blood collection tube 1, among the various parameters 11 of each type of blood collection tube 1 stored in the database 12.

The second image processing unit 7c processes the image captured by the imaging unit 6 for analyte checking according to the threshold parameter 11B in accordance with the type of blood collection tube 1 specified by the first image processing unit 7a.

The discrimination unit 7d discriminates the state of the analyte in the blood collection tube 1 on the basis of the image processed by the second image processing unit 7c. Further, the discrimination unit 7d calculates the volume of the analyte in the blood collection tube 1 from the captured images in the imaging unit 6 for analyte checking.

The details of the analyte checking in the blood collection tube 1 will be explained with reference to FIG. 4.

As shown in FIG. 4, when the blood collection tube 1 storing the sampled analyte is centrifuged, the contents are separated into a serum portion 1a, a separating agent 1b, and a blood clot portion 1c from top to bottom. The serum portion 1a has yellow colored components, the separating agent 1b has white components, and the blood clot portion is has red colored components. Among them, a portion of the serum portion 1a is used in the analyte check.

Therefore, the second image processing unit 7c uses the threshold parameter which mainly includes the yellow colored components to extract the region of the serum portion 1a. Moreover, the discrimination unit 7d calculates the average value of the color of the region of the extracted serum portion, and compares the average value to the threshold parameter to perform discrimination of the hemolytic, the chylous, and the icteric states. Further, the discrimination unit 7d, after obtaining the upper surface 24 and the lower surface 25 (separating agent upper surface) of the serum portion 1a extracted by the second image processing unit 7c, calculates the volume of serum by the liquid height 27 which is the difference between the upper surface 24 and the lower surface 25 and the inner diameter 28 of the blood collection tube.

The details of the discrimination process of the state of the analyte in the discrimination unit 7d will be explained below in FIG. 5.

In order for the discrimination unit 7d to discriminate the state of the analyte (serum portion 1a), the image captured in the second image processing unit 7c is converted to the HSV color system (hue, saturation, and value).

When the blood collection tube 1 is transparent, the serum and the separating agent are in the HS region, and is distributed as the serum 121 of the normal analyte, the serum 121 of the hemolytic analyte, and the separating agent 123 as shown in FIG. 5. However, in the case of the milky-white blood collection tube 1 (white translucent blood collection tube) as shown in FIG. 6, the serum is distributed in the direction in which the saturation is low as the serum 131 of the normal analyte, the serum 132 of the hemolytic analyte, and the separating agent 133 as shown in FIG. 5. Therefore, in the case of the milky-white blood collection tube 1, the white color is emphasized, thus, when attempting to extract the serum region with the same threshold parameters (H, S and V values) as the transparent blood collection tube 1, verification of the interface between the serum portion 1a and the white gel-like separating agent 1b is difficult, thus, there are many cases when the extraction of the serum portion 1a is unsuccessful. Specifically, there is a portion of the separating agent 1b in which the distribution of the separating agent 123 in the transparent blood collection tube 1 overlaps with the distribution of the serum 131 of the normal analyte in the milky-white blood collection tube 1, thus, the risk that the separation of the serum portion 1a from the separating agent 1b is unsuccessful is high. Further, the risk of incorrectly verifying that the state of the analyte (serum portion 1a) is a chylous state is high.

Therefore, the discrimination unit 7d captures an image of the outer appearance of the blood collection tube 1 in the imaging unit 3 for automatically verifying the blood collection tube in advance, and specifies the type of blood collection tube 1 in the first image processing unit 7a prior to the checking of the analyte check. Moreover, if a milky-white blood collection tube 1 is specified, the image processing is performed with reference to the threshold parameter 11B for the specified milky-white blood collection tube. With respect thereto, when a transparent blood collection tube 1 is specified, the image processing is performed with reference to the threshold parameter 11B for the specified transparent blood collection tube.

Next, the calculation method of the volume of the analyte in the blood collection tube 1 will be explained.

The discrimination unit 7d, after obtaining the upper surface 24 and the lower surface 25 (separating agent upper surface) of the serum portion 1a previously extracted by the second image processing unit 7c, seeks the liquid height 27 which is the difference between the upper surface 24 and the lower surface 25, and calculates the volume of the serum portion 1a of the blood collection tube 1 from the information relating to the height 27 of the obtained serum portion 1a and the information relating to the diameter of the blood collection tube 1 specified from the type of blood collection tube 1 specified by the first image processing unit 7a.

The obtained information of the volume of the serum portion 1a is used in the dispensing part 110 when dispensing the sample into the blood collection tube 1.

Returning to FIG. 2, the grip member 14 lifts the blood collection tube 1 from the holder 2 according to the lifting operation parameter 11A obtained by the calculation unit 7b of the operation control unit 101.

The details of the lifting and the accompanying rotation of the blood collection tube 1 in the grip member 14 will be explained below with reference to FIG. 7.

As shown in FIG. 7, the grip member 14 grips the blood collection tube 1 by operating an opening and closing mechanism 23. After gripping the blood collection tube 1, the tube 1 is lifted to the imaging height position of the image in the imaging unit 6 for analyte checking by the blood collection tube lifting operation mechanism 21.

A barcode label 4 is attached to the blood collection tube 1, thus, it is necessary to rotate the blood collection tube 1 so the gap of the barcode label 4 faces towards the imaging unit 6 side as shown in FIG. 8, in order to perform the imaging by the imaging unit 6 for analyte checking. Therefore, after the blood collection tube 1 is lifted by the grip member 14, the grip member 14 is rotated by the blood collection tube rotation operation mechanism 22 to perform the rotation operation of the blood collection tube 1 while performing imaging by the imaging unit 6 for analyte checking.

The blood collection tubes 1 loaded in the analyte testing automation system have different lengths. If the operation parameters for lifting all of the blood collection tubes are the same, it is necessary that the height position for grasping the blood collection tubes match with the gripping position 31 of short blood collection tubes. However, there is the problem that if the gripping height matches with the short blood collection tubes, when the long blood collection tubes are grasped by the grip member and the serum portion image is captured, an interference area 35 is produced as shown in FIG. 9, and the grip member becomes impeded, thus, the verification of the interface is difficult.

Therefore, in the embodiment, the lifting operation parameter 11B is appropriately changed according to the type of blood collection tube 1 when lifting the blood collection tube 1.

Specifically, when it is specified that the short blood collection tube 1 in which the outer appearance of the blood collection tube 1 was captured beforehand in the imaging unit 3 for automatically verifying the blood collection tube, and the type of blood collection tube 1 specified in the first image processing unit 7a is being used, the drop operation 33 to the height position and the elevation operation 34 to the blood collection tube imaging height position which grasps the blood collection tube 1 as shown in FIG. 10 and the lifting operation parameter 11A for the short blood collection tubes are used. Further, when it is specified that a long blood collection tube 1 is being used, a drop operation 37 to the height position and the elevation operation 38 to the blood collection tube imaging height position which grasps blood collection tube 1 as shown in FIG. 10 and the lifting operation parameter 11A for tall blood collection tubes are used.

Returning to FIG. 2, the imaging unit 6 for analyte checking captures an image from the side of the blood collection tube 1 in a state lifted by the grip member 14.

Next, the sequence of the processes of the operation of the analyte testing automation system of the embodiment will be explained below with reference to FIG. 11.

First, when it is verified in the operation control unit 101 by the user that the blood collection tube 1 has been loaded from the analyte loading unit 105 into the analyte pretreatment system 100 (Step S61), an image of the outer appearance of the blood collection tube 1 is captured in the imaging unit 3 for automatically verifying the blood collection tube in a state in which the blood collection tube 1 is placed in the holder 2 to specify the type of blood collection tube 1 from the image captured beforehand in the first image processing unit 7a of the operation control unit 101 (Step S62).

Then, the blood collection tube 1 is conveyed from the analyte loading unit 105 to the analyte checker 107 (Step S63).

While the blood collection tube 1 is being conveyed to the analyte checker 107, the lifting operation parameter 11A is calculated (Step S64) in the calculation unit 7b on the basis of the automatic recognition result of the blood collection tube 1 in Step S62. Moreover, the blood collection tube 1 is lifted by the grip member 14 to the imaging height with reference to the lifting operation parameter 11A obtained by the calculation unit 7b in Step S64 (Step S65). Moreover, while the blood collection tube 1 is rotated by the blood collection tube rotation operation mechanism 22, images of the blood collection tube 1 are captured by the imaging unit 6 for analyte checking (Step S66).

Further, the threshold parameter 11B is obtained from each of the parameters of database 12 on the basis of the automatic recognition result of the blood collection tube 1 in Step S62 (Step S67). Note that, Step S67 may be performed at any time after Step S62 until the next Step S68 starts.

Next, using the threshold parameter 11B obtained in Step S67, the region of the serum portion 1a is extracted from the image captured by the imaging unit 6 for analyte checking in Step S66 in the second image processing unit 7c (Step S68).

Next, the volume of serum is calculated in the discrimination unit 7d from the extraction result in Step S68 (Step S69). Further, with reference to the threshold parameter 11B, the analyte in the blood collection tube 1 is compared with the average value of the color of the serum, and whether the analyte in the blood collection tube 1 is any of the hemolytic, the chylous, or the icteric state is discriminated in the discrimination unit 7d (Step S70). In Step S70, the discrimination unit 7d confirms whether or not there is an abnormality in the shape of the analyte or the liquid quantity, and when there is an abnormality, instructions such as a redrawing of blood are displayed on the display unit of the operation control unit 101, and if there is no abnormality, the process proceeds to Step S71.

The image processing (analyte check) result in Step S70 and the image captured in Step S66 are stored in the analyte check result storage database 13 (Step S71).

If instructions such as for a redrawing of blood are received in Step S70, the user is able to take early measures by making arrangements so that a redrawing of blood may be performed.

As stated above, the first embodiment of the analyte testing automation system and the biological sample check method of the present invention automatically recognizes the type of blood collection tube 1 loaded into the system, switches the image processing threshold on the basis of this automatic recognition result, uses the threshold parameter in accordance with the blood collection tube type to perform image processing, and performs checking of the state and volume of the analyte.

By these processes, even when the transparent blood collection tube 1 was mixed with the milky cloudy blood collection tube 1, it is possible to perform image processing according to the type of blood collection tube 1, thus, the region extraction of the serum portion and the precision of the state determination of the analyte can increase. Further, the degree to which the analysis of the analyte can be performed in the automatic analyzer 200 can be discriminated, controlled so as to prioritize testing of analysis items having a higher priority, and it is possible for the user to know that the redrawing of blood is necessary by the occurrence of insufficiencies, thus, rapid and flexible testing is possible even if loaded into a system without consideration of the type of blood collection tube 1.

Therefore, even if the user performs calibration to each type of blood collection tube 1 to be used, analyte checking such as the verification of the volume of serum and the state of the analyte can be automatically and precisely performed by only setting the blood collection tube 1 in the loading position without consideration of the differences in color from the transparent blood collection tube 1 as shown in FIG. 4 to the clouded milky-white as shown in FIG. 6, and the differences in the shape of the blood collection tube 1 such as the length of the tube and the inner diameter of the tube as shown in FIG. 9 and FIG. 10, and the blood collection tube 1 can be loaded in the analyte testing automation system without it being necessary for the user to perform operations which require time and effort such as calibration.

Further, the blood collection tube can be grasped and lifted to a suitable height by switching the lifting operation for checking the state and volume of analyte on the basis of the automatic recognition result, determining the mechanical operation parameter in accordance with the blood collection tube type, and lifting by grasping the blood collection tube 1, thus, it is possible that the grip member 14 does not cause interference in the imaging area when capturing an image, and it is possible to control the interference due to the holder 2 by lifting, thus, disturbances when checking the state can be minimized and an improvement of the check information can be ensured.

Further, parameter 11 is set in advance in accordance with all of the types of blood collection tubes 1 at the time the device is shipped, and thus, is an advantageous point in that it is not necessary for the user to perform calibration by the parameters already stored in the database 12.

Note that, it is possible that the database 12 and the database 13 exist within the operation control unit 101. Further, these databases 12 and 13 may exist in a server through a network.

Further, it is not always necessary that the first image processing unit 7a, the calculation unit 7b, the second image processing unit 7c, and the discrimination unit 7d are present within the operation control unit 101, and the above features may exist within the analyte checker 107, or may exist elsewhere, and the imaging unit 3 for automatically verifying the blood collection tube and the imaging unit 6 for analyte checking, the operation control unit 101, and the grip member 14 may be communicatively connected.

In the abovementioned embodiment, the type of blood collection tube was automatically verified by the shape of the blood collection tube 1, the color of the cap on the basis of the captured image, and the methods to be specified were explained, but the method for specifying the type of blood collection tube is not limited thereto. For example, the type of blood collection tube may be specified by detecting feature points on the outer appearance of the blood collection tube 1 with a single, or, a plurality of beam sensors, a reflection type sensor, and the like, and the color of the cap may even be verified by the change of the optical reflectance. Further, the information relating to the type of blood collection tube may be recorded in a storage medium such as a barcode label or an RFID tag provided on the analyte container or the holder, and may be stored in a device side storage unit in association with the verification information stored in the barcode or the RFID tag.

Further, the discrimination process of the serum portion 1a in the discrimination unit 7d has been explained regarding the case when there are two types of blood collection tubes 1, a transparent tube and a milky-white tube, but the type of blood collection tube 1 is not limited thereto, and even in the cases of other colors and other materials, by seeking the threshold parameter 11B in accordance with each color and material on the device maker's side and storing in database 12 in advance, there is the possibility that the tube corresponds to various types of blood collection tubes 1.

The parameters 11 set for each type of blood collection tube are not limited to the lifting operation parameter 11A and the threshold parameter 11B. Parameters may be used in the prevention of the loss of interface recognition due to the similarity of the colors of the chylous analyte and the separating agent by registering information such as the presence of a separating agent and the presence of a label, and may be used in threshold correction when the color of the serum appears to be dark due to the influence of the label. Further, the parameters may be used in the judgment of whether or not the filling quantity in the blood collection tubes is sufficient by registering the information of the graduation markings on the container itself.

<Second Embodiment>

A second embodiment of the analyte testing automation system and the biological sample check method of the present invention will be explained using FIG. 12.

The analyte testing automation system in the second embodiment is the same as the analyte testing automation system of the first embodiment, with the exception that the imaging unit 6 for analyte checking also serves as the imaging unit 3 for automatically verifying the blood collection tube for which images of the blood collection tube 1 loaded in the analyte testing automation system were captured, thus, the details have been omitted.

Figure 12:
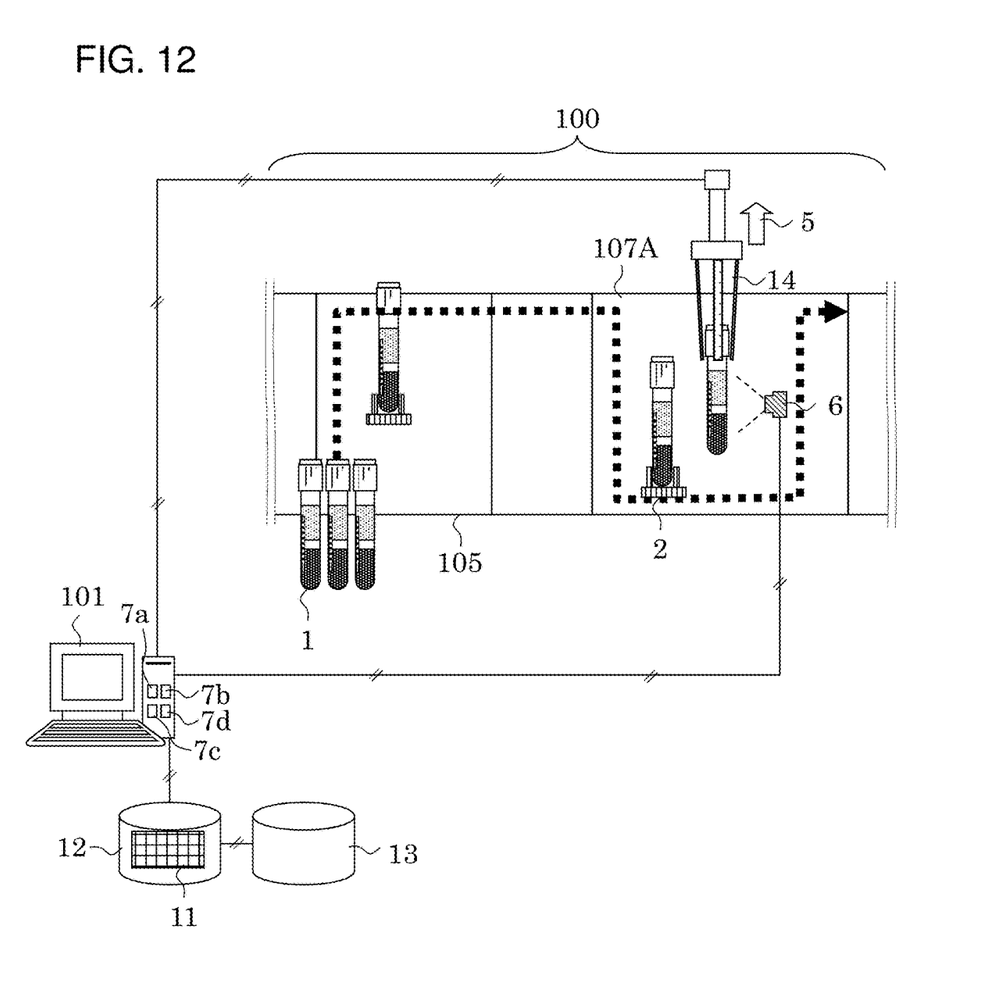
FIG. 12 is a drawing showing the overview of the configuration of the analyte testing automation system in a second embodiment of the present invention.

FIG. 12 is a drawing showing the overview of the configuration of the analyte testing automation system in the second embodiment of the present invention.

As shown in FIG. 12, the analyte testing automation system of the second embodiment does not provide an imaging unit 3 for automatically verifying the blood collection tube in the analyte loading unit 105, and the imaging unit 6 for analyte checking provided in the analyte checker 107 is a configuration which also serves as the imaging unit 3 for automatically verifying the blood collection tube which captures an image of the blood collection tube 1 loaded within the analyte pretreatment system 100.

In the embodiment, when the blood collection tube 1 is loaded in the analyte loading unit 105, if the blood collection tube 1 was placed in the holder 2, it is conveyed to the analyte checker 107, an image of the blood collection tube 1 is captured by the imaging unit 6 for analyte checking in a state in which it was placed in the holder 2 prior to the lifting operation by the grip member 14, and the type of blood collection tube 1 is automatically verified by the first image processing unit 7a and the calculation unit 7b. The lifting parameter 11A is obtained in accordance with the blood collection tube 1 using this result and the threshold parameter 11B of the image processing is obtained. Then, the lifting process of the blood collection tube 1 is performed by the grip member 14, and the subsequent processes are the same as in the first embodiment.

The second embodiment of the analyte testing automation system and the biological sample check method of the present invention can obtain almost the same effect as with the first embodiment of the analyte testing automation system and the biological sample check method. Further, according to this embodiment, the imaging unit for analyte checking is used in the external appearance recognition of the blood collection tubes without providing an exclusive imaging unit, thus, the image capturing mechanism can be reduced and the miniaturization and price reduction of the device is possible.

Further, the state and the volume of the sample in the blood collection tubes may be grasped by the analyte checker itself, and thus, the analyte checker is a module suitable for adding to an existing analyte pretreatment system.

<Third Embodiment>

A third embodiment of the analyte testing automation system, the biological sample check module, and the biological sample check method of the present invention will be explained using FIG. 13.

The analyte testing automation system in the third embodiment is the same as the analyte testing automation system of the first embodiment, with the exception that the imaging unit 3 for automatically verifying the blood collection tube was provided in the analyte checker, thus, the details have been omitted.

Figure 13:
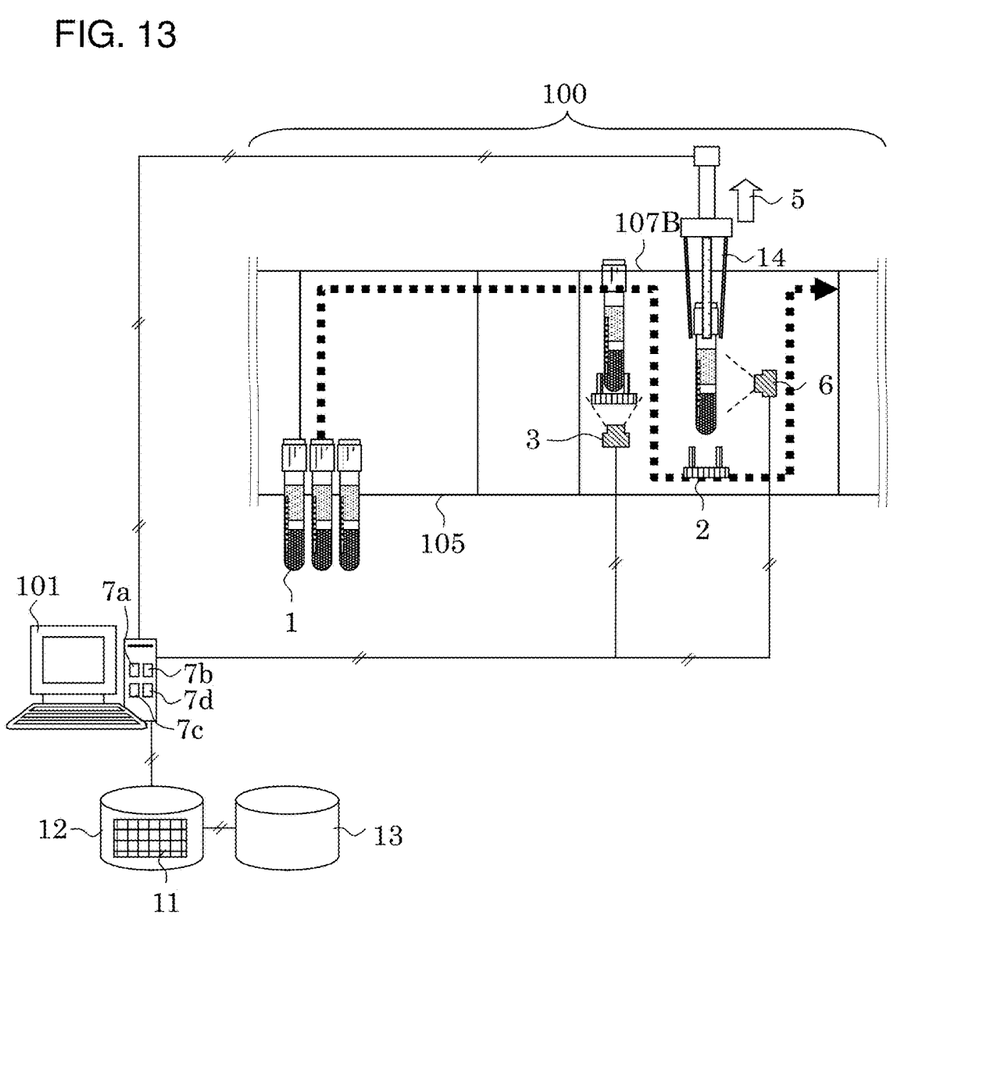
FIG. 13 is a drawing showing the overview of the configuration of the analyte testing automation system in a third embodiment of the present invention.

FIG. 13 is a drawing showing the overview of the configuration of the analyte testing automation system in the third embodiment of the present invention.

As shown in FIG. 13, in the analyte testing automation system of the third embodiment, the imaging unit 3 for automatically verifying the blood collection tube which are loaded in the analyte loading unit 105 and which captures images of the blood collection tube 1 which are loaded in the analyte checker 107 is provided on the inlet side in the analyte checker 107 of the blood collection tube 1 which is conveyed to the analyte checker 107.

The other configurations and operation processes are the same as the analyte testing automation system of the first embodiment.

The third embodiment of the analyte testing automation system, the biological sample check module, and the biological sample check method of the present invention can obtain almost the same effect as with the first embodiment of the analyte testing automation system, the biological sample check module, and the biological sample check method.

Further, it is possible to grasp the state and the volume of the sample in the blood collection tube with the biological sample check module itself in the same manner as the second embodiment, and thus, the biological sample check module is a module suitable for adding to an existing analyte pretreatment system.

<Other Embodiments>

Note that, the present invention is not limited to the aforementioned embodiments, and various modifications and applications are possible. The embodiments above have been explained as detailed examples helping this invention to be better understood. The present invention, when embodied, is not necessarily limited to any embodiment that includes all the structures described above.

For example, the abovementioned analyte checker and volume checking module for realizing an analyte check function prevents the wasteful loss of consumables such as the analyte and dispensing chips, and thus, are desirably provided between the centrifuge unit 106 and the dispensing part 110.

LIST OF REFERENCE SIGNS

1 . . . blood collection tube,
2 . . . holder,
3 . . . imaging unit for automatically verifying the blood collection tube,
6 . . . imaging unit for analyte checking,
7a . . . first image processing unit,
7b . . . the calculation unit,
7c . . . second image processing unit,
7d . . . discrimination unit,
11 . . . various parameters for each type of blood collection tube,
11A . . . lifting operation parameter,
11B . . . threshold parameter,
12 . . . lifting operation parameter and threshold parameter storage database,
13 . . . analyte check result storage database,
14 . . . grip member,
21 . . . blood collection tube lifting operation mechanism,
22 . . . blood collection tube rotation operation mechanism,
23 . . . grip member opening and closing mechanism,
24 . . . serum portion upper surface,
25 . . . separating agent portion upper surface,
26 . . . blood clot portion upper surface,
27 . . . serum portion liquid height,
28 . . . blood collection tube inner diameter,
31 . . . height position for grasping blood collection tube (for low blood collection tubes),
32 . . . blood collection tube imaging height position,
33 . . . drop operation to height position for grasping blood collection tube (for low blood collection tubes),
34 . . . elevation operation to blood collection tube imaging height position (for low blood collection tubes),
35 . . . interference area of grip member,
36 . . . height position for grasping blood collection tube (for tall blood collection tubes),
37 . . . drop operation to height position for grasping blood collection tube (for tall blood collection tubes),
38 . . . elevation operation to blood collection tube imaging height position (for tall blood collection tubes),
100 . . . analyte pretreatment system,
101 . . . operation control unit,
102 . . . plug part,
103 . . . analyte storage unit,
104 . . . empty holder stocker part,
105 . . . analyte loading unit,
106 . . . centrifuge unit,
107 . . . analyte checker (biological sample check module),
108 . . . opening unit,
109 . . . aliquot sample test tube preparation unit,
110 . . . dispensing part,
111 . . . transfer unit,
121 . . . distribution range of normal analyte,
122 . . . distribution range of hemolytic analyte,
123 . . . distribution range of separating agent, 131 . . . distribution range of normal analyte in milky-white blood collection tube,
132 . . . distribution range of hemolytic analyte in milky-white blood collection tube,
133 . . . distribution range of separating agent in milky-white blood collection tube,
200 . . . automatic analyzer.

The invention claimed is:

1. An analyte testing automation system comprising:
a camera configured to capture an image of a container, in which a biological sample is stored, from a side thereof;
a grip member configured to grasp and lift the container;
a database which stores a plurality of different container types that specify a plurality of different lifting operation parameters and a plurality of different threshold parameters;
a controller coupled to the camera and the grip member, and programmed to:
control the camera to capture a first image of the container,
determine a container type of the container from among the different container types stored in the database according to a length, a diameter and a cap color of the container in the first image,
determine a lifting operation parameter and a threshold parameter of the container from the different lifting operation parameters and the different threshold parameters in the database specified by the determined container type,
control the grip member to lift the container to a predetermined height specified by the lifting operation parameter,
capture a second image of the container in a state where the container is lifted to the predetermined height by the grip member,
compare the second image to one or more predetermined color values specified by the threshold parameter, and
determine a state of an analyte in the biological sample in the container from the comparison.

2. The analyte testing automation system according to claim 1,
wherein the grip member is further configured to lift the container from a holder,
the controller is further programmed to control the camera to capture the first image while the container is held by the holder, and the first image and the second image are captured by the camera from the side of the container.

3. The analyte testing automation system according to claim 1,
wherein the different container types include a transparent container and a white translucent container.

4. The analyte testing automation system according to claim 1,
wherein the controller is further programmed to discriminate a position of a liquid interface of the biological sample, a presence of a separating agent or a presence of a label from the second image.

5. The analyte testing automation system according to claim 1, wherein the determined state is one of a hemolytic state, a chylous state and icteric state.

6. The analyte testing automation system according to claim 1, wherein a barcode label is attached to the container,
the gripping member is further configured to rotate the container, and
after capturing the first image and before capturing the second image, the controller is further configured to control the grip member to rotate the container until a gap in the barcode label faces the camera.

7. A biological sample check module for checking a biological sample stored in a container, comprising:
a camera configured to capture an image of the container, in which the biological sample is stored, from a side thereof;
a grip member configured to grasp and lift the container; and
a controller programmed to control the camera to:
capture a first image of the container,
determine a container type of the container from a length, a diameter and a cap color of the container in the first image,
determine a lifting operation parameter and a threshold parameter of the container specified by the determined container type,
control the grip member to lift the container to a predetermined height specified by the lifting operation parameter,
capture a second image of the container in a state where the container is lifted to the predetermined height by the grip member,
compare the second image to one or more predetermined color values specified by the threshold parameter, and
determine a state of the biological sample in the container from the comparison.

8. The biological sample check module according to claim 7, wherein the determined state is one of a hemolytic state, a chylous state and icteric state.

9. The biological sample check module according to claim 7, wherein a barcode label is attached to the container,
the gripping member is further configured to rotate the container, and
after capturing the first image and before capturing the second image, the controller is further configured to control the grip member to rotate the container until a gap in the barcode label faces the camera.

10. A biological sample check method, comprising:
capturing a first image of a container in which a biological sample is stored from a side thereof;
determining a container type of the container among a plurality of different container types from a length, a diameter and a cap color of the container in the first image;
determining a lifting operation parameter and a threshold parameter of the container specified by the determined container type;
controlling a grip member to lift the container to a predetermined height specified by the lifting operation parameter;
capturing a second image of the container from a side thereof in a state where the container is lifted to the predetermined height by the grip member;
comparing the second image to one or more predetermined color values specified by the threshold parameter, and
determining a state of the biological sample in the container from the comparison.

11. The biological sample check method according to claim 10,
wherein the first image is captured while the container is held by a holder and the second image is captured while the grip member lifts the container to the predetermined height from the holder.

12. The biological sample check method according to claim 10, wherein the determined container type is one of a transparent container or a white translucent container.

13. The biological sample check method according to claim 10, further comprising:
determining a position of a liquid interface of the biological sample, a presence of a separating agent, or a presence of a label from the second image.

14. The biological sample check method according to claim 10, wherein a barcode label is attached to the container, and
after capturing the first image and before capturing the second image, the grip member rotates the container until a gap in the barcode label faces the camera.

15. The biological sample check method according to claim 10, wherein the determined state is one of a hemolytic state, a chylous state and icteric state.

* * * * *